United States Patent [19]

Hsu

[11] Patent Number: 4,632,913
[45] Date of Patent: Dec. 30, 1986

[54] BORON PHOSPHATE CATALYST FOR THE PRODUCTION OF DIENES FROM ALDEHYDES

[75] Inventor: Wen-Liang Hsu, Akron, Ohio

[73] Assignee: The Goodyear Tire & Rubber Company, Akron, Ohio

[21] Appl. No.: 821,294

[22] Filed: Jan. 22, 1986

Related U.S. Application Data

[62] Division of Ser. No. 761,728, Aug. 2, 1985, Pat. No. 4,587,372.

[51] Int. Cl.$^4$ .................. B01J 21/02; B01J 21/18; B01J 22/24
[52] U.S. Cl. ............................. 502/202; 502/174; 502/200
[58] Field of Search .................. 502/174, 200, 202

[56] References Cited

U.S. PATENT DOCUMENTS

| | | | |
|---|---|---|---|
| 3,030,314 | 4/1962 | Knowtton et al. | 502/174 |
| 3,395,984 | 8/1968 | Collins | 502/202 X |
| 3,849,335 | 11/1974 | Immel et al. | 502/200 |
| 4,524,233 | 6/1985 | Hsu et al. | 502/202 X |
| 4,547,614 | 10/1985 | Vorene | 585/606 |

FOREIGN PATENT DOCUMENTS

| | | | |
|---|---|---|---|
| 2163396 | 7/1973 | Fed. Rep. of Germany | 585/606 |
| 1385348 | 2/1975 | United Kingdom | 585/606 |
| 2093060A | 8/1982 | United Kingdom | |
| 476070 | 3/1980 | U.S.S.R. | |

OTHER PUBLICATIONS

The Rule of Surface Activity of BP 04 in the Activity and Selectivity of the Dehydration of Alcohols, S. S. Jewur et al., J. of Cat. 57, pp. 167–176, 1979.
Bol'Shakov et al, Prom-St. Sint Kewich, 1980 (8), 2–4.

*Primary Examiner*—Andrew H. Metz
*Assistant Examiner*—William G. Wright
*Attorney, Agent, or Firm*—D. O. Nickey

[57] ABSTRACT

This invention is concerned with improved boron phosphate dehydration catalysts. More specifically this invention is directed to a process for the conversion of an aldehyde to a diolefin comprising contacting an aldehyde of 4 to 6 carbon atoms in the vapor phase with a catalyst comprising boron phosphate wherein the boron phosphate has been treated with an ammonium carbonate or bicarbonate salt prior to calcination. This invention is also concerned with a large pore catalyst for dehydration reactions wherein the improvement comprises the use of a catalyst with a molar ratio of P/B of about 1.0 modified with from 0.1 to 10 mole percent, based on moles of boron, of a carbonate salt selected from $(NH_4)_2CO_3$ and $NH_4HCO_3$.

2 Claims, 4 Drawing Figures

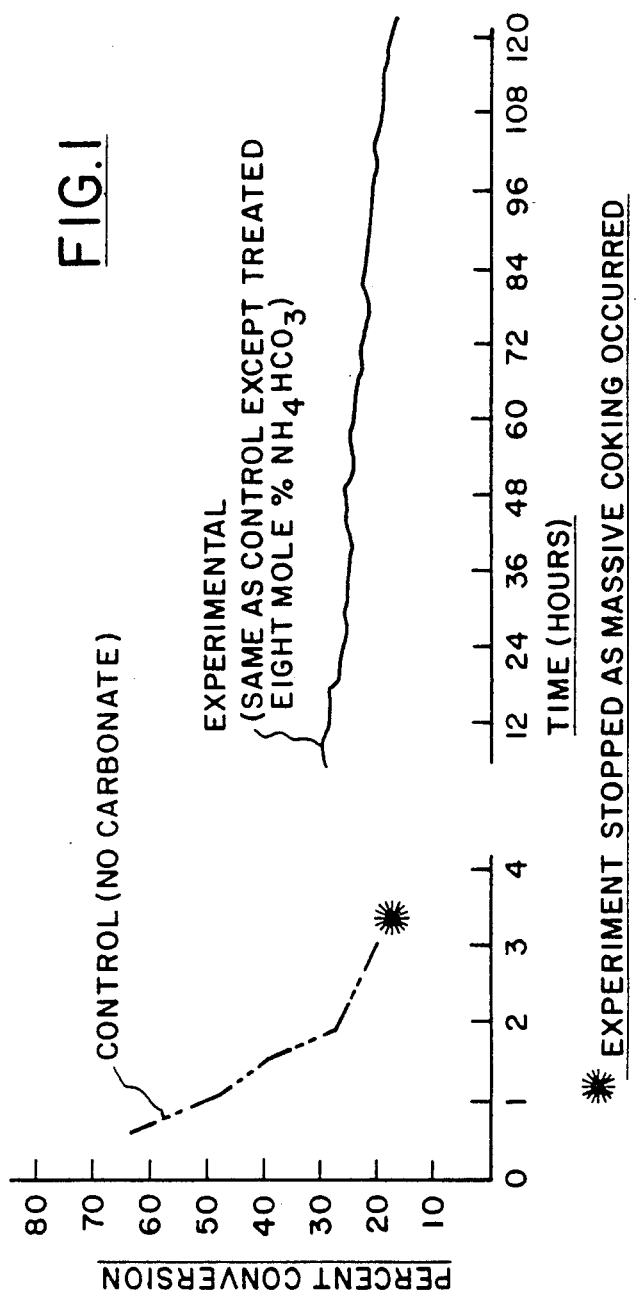

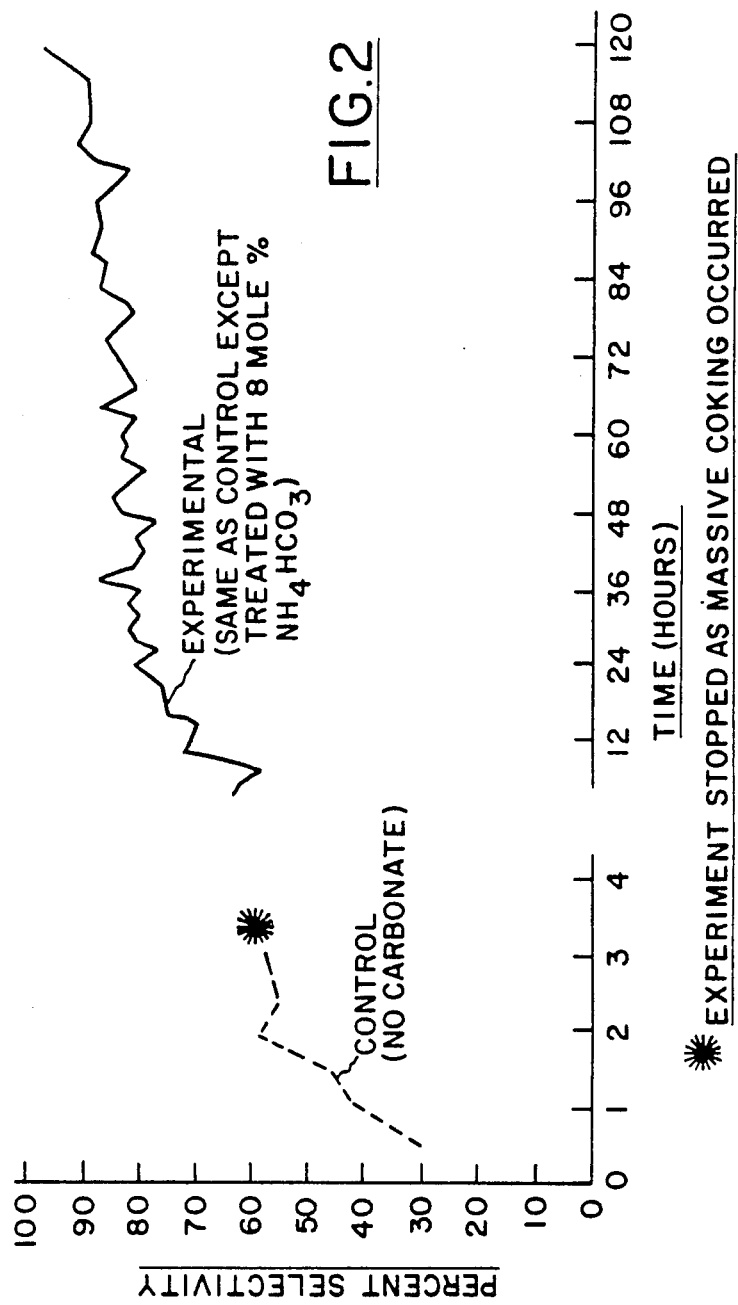

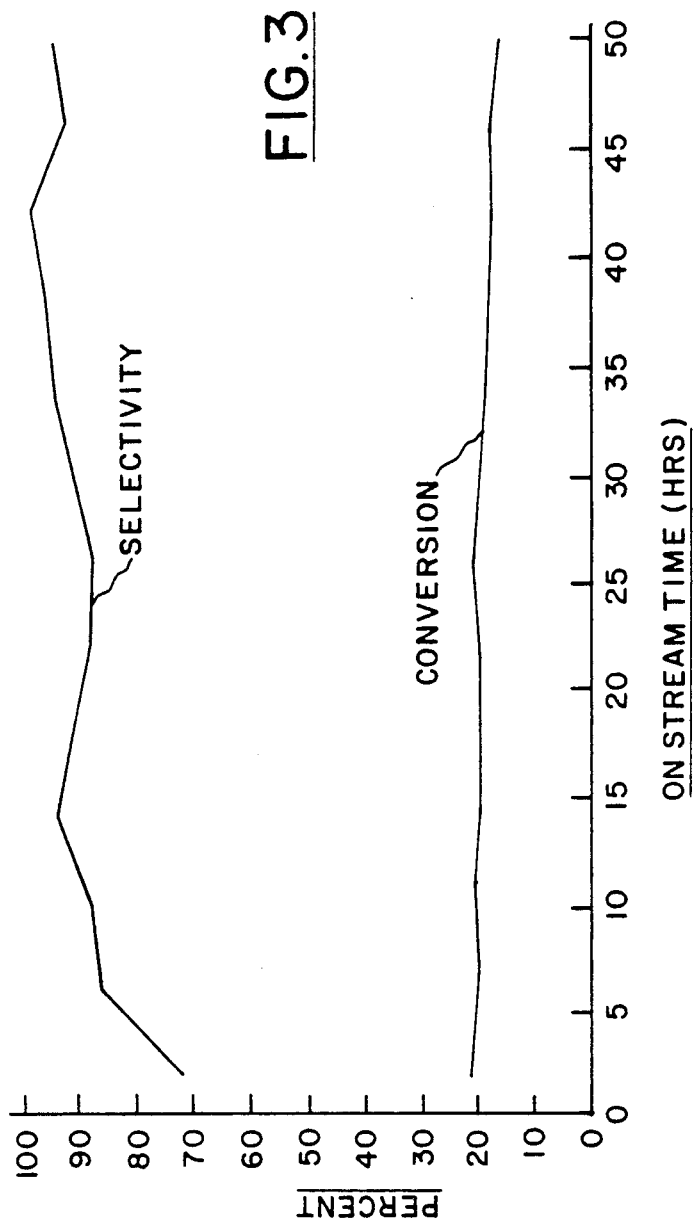

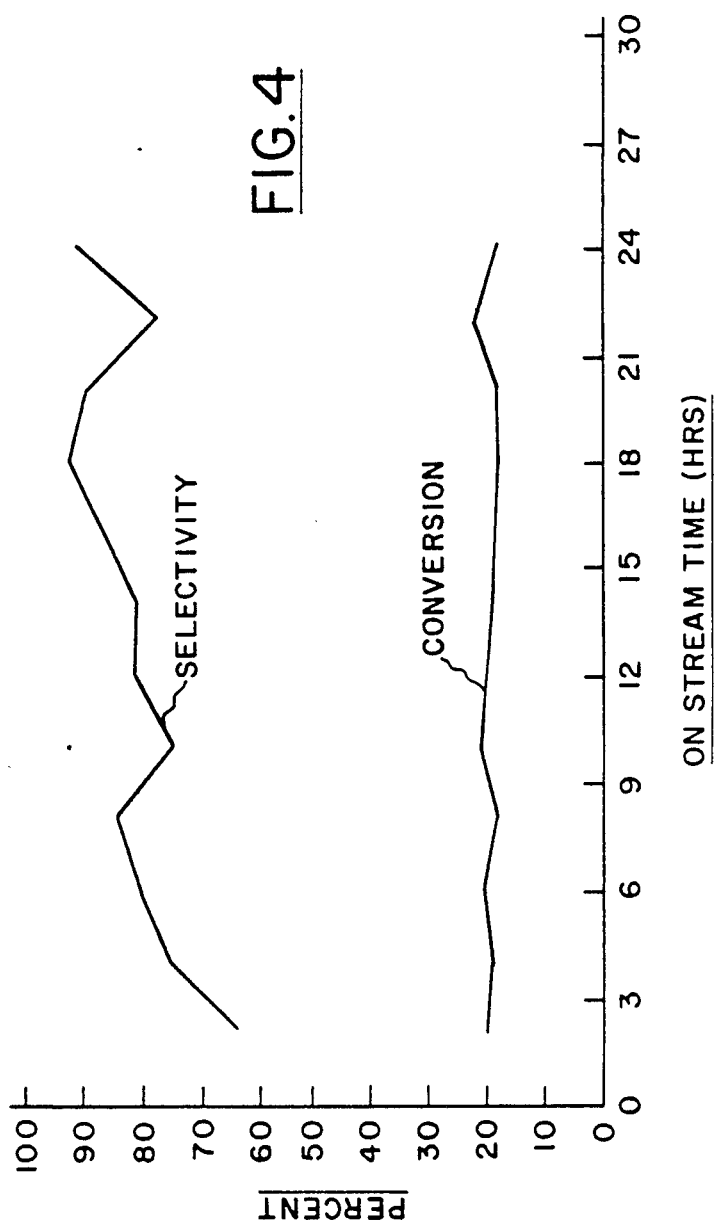

BORON PHOSPHATE CATALYST FOR THE PRODUCTION OF DIENES FROM ALDEHYDES

This is a divisional of application Ser. No. 761,728, filed on Aug. 2, 1985, allowed on Dec. 10, 1985, now U.S. Pat. No. 4,587,372.

TECHNICAL FIELD

This invention relates to a process for converting aldehydes to dienes. More specifically, this invention is concerned with an improved large pore catalyst for the conversion of 2-methylbutanal (2MBA) to isoprene.

BACKGROUND ART

Dienes, especially isoprene, are useful as monomers for the manufacture of synthetic rubbers. Isoprene is primarily used to make cis-polyisoprene which is a stereospecific rubber having the same segmeric unit as natural rubber. Several fundamental processes have been used to construct the isoprene $C_5$ skeleton from smaller carbon units. These processes are not commercially accepted in that there are numerous problems associated with each particular synthesis route. One route involves condensing acetylene and acetone followed by hydrogenation and dehydration. Another route involves as a first step the reaction between formaldehyde and isobutylene, and in a subsequent step the intermediate derivative is catalytically cracked at elevated temperatures. See for example, French Pat. No. 1,294,716; Chem. Abstracts 57:15309.

European Patent Application No. 80449 based on U.S. application No. 315,803 discloses the synthesis of isoprene from linear butenes wherein mixed linear butenes are catalytically isomerized to a mixture of cis- and trans-butene-2, and then hydroformylating the butene-2 mixture to 2-methylbutanal (2MBA) in the presence of a homogeneous rhodium catalyst and organic ligand. The 2MBA is then dehydrated to isoprene in the presence of acidic heterogeneous catalysts at elevated temperatures. This European patent application discloses a preferred catalyst for the dehydration step as a boron phosphate which is described in British Pat. No. 1,385,348. The dehydration reaction is endothermic, and under preferred conditions, the reaction is performed in the vapor phase over a fixed bed of catalyst at elevated temperatures from about 200° to about 400° C. This patent application, however, does not disclose the length of time the catalyst performs at such selectivities and conversions (lifetime). Commercial production of isoprene via the aldehyde dehydration route has not been established since the dehydration catalyst is known to have short lifetimes which limit its utility in commercial applications.

U.K. Pat. No. 1,385,348 relates to the conversion of aldehydes to dienes with conjugated double bonds. This British patent recites that particularly preferred acid dehydration catalysts are mixed acid anhydrides, for example, boron phosphate, silicoborate or silicotitanate. In these mixed acid anhydrides the two acid components may be present in a stoichiometric ratio or, alternatively, one of the two components may be present in excess. Boron phosphate is particularly preferred. Further, U.K. Pat. No. 1,385,348 states that it is advantageous for the boron phosphate to contain an excess of from 1 to 10% by weight of phosphoric acid. The examples provided in the British patent utilize a boron phosphate containing an excess of phosphoric acid. The examples recite results with conversions as high as 92.9% and selectivities as high as 68.4%. However, there is no discussion or information relating to the duration of such conversions and selectivities and/or the number of regenerations required during any particular time period.

U.K. Pat. No. 2,093,060 relates to the preparation of substituted dienes, especially isoprene, from a corresponding carbonyl compound in which magnesium ammonium phosphate or its decomposition products are used as the dehydration catalyst. However, there is no data relating to the duration of catalyst activity.

A disadvantage associated with known catalysts to dehydrate aldehydes is that catalyst life depends on many factors which include catalyst composition and structure, catalyst activity, operating temperatures and coke deposition. Coke deposition is understood to denote coke (carbonaceous) deposits formed on the catalyst during the dehydration reaction. As stated earlier, no commercial process based on said technique has been developed so far, since there is no catalyst with selectivity and stability to justify a commercial process.

The use of boron phosphate as a catalyst for the dehydration of alcohols such as 2-butanol and 2-methyl-2-butanol is known. See Jewur and Moffat, *Journal of Catalysis*, 57, 167-176 (1979). The problems associated with an aldehyde dehydration are different and more difficult to overcome than those found in alcohol dehydrations. For example, the boron phosphate dehydration of 2-methyl-2-butanol yields only 2-methyl-2-butene and 2-methyl-1-butene, while dehydration of 2MBA yields primarily methylisopropylketone, 2-methyl-2-butene, 2-methyl-1-butene and isoprene. It is the production of the conjugated diolefin, isoprene, that makes the aldehyde dehydrations so difficult, since this highly reactive monomer is known to form dimers and/or polymerize in the presence of acid catalysts.

In addition, aldehydes such as 2MBA are known to undergo aldol condensation. This is a reaction between two molecules of an aliphatic aldehyde whereby a 3-hydroxyaldehyde is formed. Dehydration of the 3-hydroxyaldehyde results in the formation of terpenes, a highly undesirable by-product that can coke and deactivate the catalyst. Due to these and other differences, catalysts suitable for long term dehydration of alcohols have not been found acceptable for aldehyde dehydration.

One aspect of this invention is directed to the use of an ammonium carbonate which is placed in intimate physical admixture with the boron phosphate during its preparation and then volatilized during calcination of the catalyst. The prior art does not suggest or disclose that the use of an ammonium carbonate in a boron phosphate catalyst will unexpectedly enhance the viable lifetime of the catalyst in a 2MBA to isoprene dehydration. Specifically, the instant invention is directed to an ammonium carbonate modification wherein the ammonium carbonate is added during the boron phosphate paste preparation and then volatilized during calcination. The ammonium carbonate is added in the range of 0.1 to 10 mole percent per mole of boron.

U.S. Pat. No. 4,524,233, issued June 18, 1985, with the instant inventor listed as a co-inventor therein is herein incorporated by reference.

The instant invention provides a catalyst of high selectivity and low coke deposition in conjunction with extended catalyst lifetimes. The prior art does not suggest or disclose a catalyst for the dehydration of aldehydes to dienes wherein a boron phosphate is modified with from 0.1 to 10 mole percent of ammonium carbonate and/or ammonium bicarbonate. The boron phosphate/ammonium carbonate mixture is then calcined prior to use.

DISCLOSURE OF THE INVENTION

There is disclosed a process for the conversion of an aldehyde of 4 to 6 carbon atoms to the corresponding diene which comprises contacting the aldehyde in the vapor phase at a temperature of from 200° to 400° C. with a boron phosphate catalyst, said catalyst characterized in that the molar ratio of phosphorous (P) to boron (B) (P/B) is about 1.0; is in admixture with from 0.1 to 10 mole percent, based on moles of boron, of ammonium carbonate and/or ammonium bicarbonate; the admixture is calcined at a temperature from 300° C. to 500° C.

There is also disclosed a process of preparing isoprene which comprises passing 2-methylbutanal in the vapor phase over a boron phosphate dehydration catalyst, the improvement comprising: a catalyst which has been treated with ammonium carbonate or ammonium bicarbonate.

There is further disclosed an improved catalyst for aldehyde dehydrations, the improvement characterized in that boron phosphate is combined with from 0.1 to 10 mole percent of ammonium carbonate and then calcined.

In addition, there is disclosed a process for the conversion of an aldehyde to the corresponding diene which comprises contacting the aldehyde in the vapor phase at a temperature of from 200° to 400° C. with a boron phosphate catalyst, the improvement characterized in that (1) the boron phosphate catalyst is prepared by (a) combining phosphoric acid and boric acid;
(b) at such ratios that the molar ratio of P/B is less than 1.1 but more than 0.9;
(c) admixing the boron phosphate with from 0.1 to 10 mole percent based on moles of boron, of an ammonium carbonate, selected from $(NH_4)_2CO_3$ and $NH_4HCO_3$;
(d) calcining the admixture in air at a temperature of from 300° to 500° C. for 1 to 6 hours.

The use of tailored surface characteristics in a catalyst or catalytic support can sometimes result in increased activity, selectivity, or lifetime for a given catalyst. It is commonly accepted that in order to achieve large pore sizes, the surface area must be reduced by either sintering of the small pores or other such surface-destructive means. See for example Newsome, J. W., Heiser, H. W., Russell, A. S. and Stumpf, H. C., "Alumina Properties", Aluminum Company of America, Pittsburgh, 1960. Since in catalytic reactions it is the surface area available to the reactants that determines reactivity, it is important to maximize both surface area and pore size to obtain the highest catalytic activity.

In accordance with the instant invention, a boron phosphate catalyst ($BPO_4$), with a phosphorus to boron ratio of 1 (P/B=1) was prepared with inclusion of 5 mole percent of ammonium carbonate. Higher porosity, after calcination at 400° C., was realized for this $BPO_4$ catalyst since the large ammonium carbonate molecule decomposes and volatilizes during calcination, thereby leaving a large void or pore.

The catalysts of this invention exhibit excellent 2MBA dehydration results. 2MBA conversion dropped about 2% (23 to 21%) in 60 hours while an unmodified $BPO_4$ [no $(NH_4)_2CO_3$] deactivated rapidly (conversion dropped from 20 to 8% in 14 hours).

It is speculated that the stability of the instant improved catalyst can be attributed to the "large pore" effect and/or the neutralization of some super acid sites of $BPO_4$ by the ammonium ion.

It has been found that dienes can be obtained with advantage from the corresponding aldehydes by contacting the aldehyde with a boron phosphate dehydration catalyst which has been treated with an ammonium carbonate prior to calcination.

Examples of the aldehydes suitable for use in the process according to the invention include 2-methylbutanal, 2,3-dimethylbutanal and 2- or 3-ethylbutanal. 2-Methylbutanal (2-MBA) is particularly preferred.

The following materials are mentioned as examples of dienes which can be produced by the process according to the invention: 1,3-butadiene, isoprene, 1,3-hexadiene, 2,3 or 4-methyl-1,3-pentadiene, 2,3-dimethylbutadiene and 2-ethyl-1,3-butadiene.

The process according to the invention is generally carried out at a temperature from 200° to 400° C. with 275° to 350° C. being preferred. The process can be carried out at ambient pressure, for example, by vaporizing the aldehydes and passing them over the catalyst with or without a carrier gas. Inert gases such as nitrogen, carbon dioxide or hydrocarbons, especially saturated hydrocarbons, have proved to be of particular advantage as carrier gases. The instant invention can be carried out under reduced pressure or super atmospheric pressure.

The dehydration catalysts, according to the invention, are boron phosphates wherein the initial molar ratio of P/B is about 1.0. It has been discovered that during the use of these catalysts, irrespective of the initial P/B ratio, the ratio of P/B approaches and stabilizes at about 1.0.

The ammonium carbonates useful in this invention are $(NH_4)_2CO_3$ and $NH_4HCO_3$. Carbonates are the salts of the weak acid, carbonic acid, $H_2CO_3$. The bicarbonates are formed by replacing only one of the two hydrogen atoms in carbonic acid. These ammonium carbonates are readily available and known to chemists.

The catalysts of the instant invention are synthesized via the paste method. In the paste method the amount of reagent grade 85% phosphoric acid required to give the desired mole ratio is placed in a glass reactor, heated to 70° C. and powdered reagent grade orthoboric acid is added slowly with stirring. When a thick paste forms the ammonium carbonate is added (after about 30 mins.). After five hours the heat is removed and the resultant paste is spread over the inner surface of a glass tube and heated to 110° C. in air for 16 hours. The white solid is chipped from the tube and stored in tightly sealed glass bottles. Prior to use the sample was ground, sieved through a 20–35 mesh sieve, and then calcined.

The catalyst of this invention is ammonium carbonate modified. Ammonium carbonate modification means the addition of $NH_4HCO_3$ and $(NH_4)_2CO_3$ during the boron phosphate preparation to moderate surface acidity and pore size of the catalyst. The ammonium carbonate is added during the boron phosphate preparation at levels ranging from 0.1 to 10 mole percent based on moles of boron. When adding the ammonium carbonate it is preferred to add solid salt directly to the $BPO_4$ paste. One skilled in the art will realize that it may be added in the aqueous form; however, no advantage is realized as the water of solution must be removed.

The catalyst can be used both in piece form (pelletized) in a fixed bed reactor or a fluidized bed reactor, in the form as prepared or the catalyst can be applied to an inert supporting material.

The dimensions of the catalyst bed are governed by the type of reactor used. The reactor is packed with catalyst particles in the form of granules, cylinders, pellets or spheres with an average diameter of the individual particles of from 2 to 12 mm, more particularly from 4 to 8 mm. In the case of a fluidized bed reactor, the catalyst is in the form of particles with dimensions of from 20 to 200 microns, preferably from 40 to 80 microns. The fixed bed reactor is preferably used in the instant process with or without the use of a carrier gas.

An advantage of the process of the instant invention is that the mild reaction conditions enable both the starting material and the reaction product to be sparingly treated, and this is reflected in the high selectivity of the reaction.

The instant invention has proved to be advantageous in that lesser amounts of tar are formed during the dehydration. In the presence of catalysts previously used for aldehyde dehydrations, for example, an aluminum silicate or heretofore used boron phosphates, tar formation occurs to such an extent that after reacting for 30 to 60 minutes there is a substantial decrease in both activity and selectivity of the catalyst. In order to regenerate such coked catalysts, the deposits would have to be burned off and after several regenerations, the catalyst may be totally useless.

BRIEF DESCRIPTION OF DRAWINGS

The invention and the advances over the art are easily understood from the accompanying figures which are graphs that set out percent conversion or selectivities against reaction time for several experiments. The reactor system used to generate the data contained in the Figures is described infra. The experimental catalysts were prepared generally as described herein, calcined, placed in the reactor system and tested for conversion of 2MBA to isoprene. All the experiments were conducted at an LHSV of 2.25 and at 275° C.

FIG. 1: Conversion of 2MBA—$BPO_4$ Catalyst With P/B Molar Ratio of 1.0 With and Without Carbonate—sets out percent conversion against reaction time in hours for a boron phosphate catalyst having ammonium carbonate modification of 8 mole percent against a control. The graph readily points out that the ammonium carbonate treatment provided a catalyst that did not deactivate (drop in conversion) as rapidly as the control.

FIG. 2: Selectivity to Isoprene—$BPO_4$ Catalyst With P/B Molar Ratio of 1.0 With and Without Carbonate—sets out percent selectivity against reaction time in hours for a boron phosphate catalyst treated with 8 mole percent $NH_4HCO_3$ based on moles of boron prior to calcination. It is evident that selectivity to isoprene is enhanced when ammonium carbonate is used to modify the catalyst.

FIG. 3: Selectivity and Conversion for $BPO_4$ catalyst with 4 mole % $NH_4HCO_3$.

FIG. 4: Selectivity and Conversion for $BPO_4$ catalyst with 4.5 mole % $NH_4HCO_3$.

BEST MODE FOR CARRYING OUT THE INVENTION

Catalyst Preparation

Generally, the boron phosphate catalyst is prepared by adding phosphoric acid to a resin kettle. The resin kettle is equipped with a paddle stirrer, thermometer and heated to 70° C. $H_3BO_3$ is charged to the resin kettle and then stirred for about 30 minutes or until a thick paste forms. After about 30 minutes the ammonium carbonate is added. Heating at 70° C. continues for an additional five hours. The thick paste is dried in an oven overnight or about 16 hours. The next day the finished catalyst is screened to a mesh of 20–35 and then calcined in air at 300°–500° C. for 1 to 6 hours. This same procedure was used to prepare numerous catalysts of varying carbonate content and the controls.

Experimental

Boric acid powder ($H_3BO_3$) and phosphoric acid ($H_3PO_4$; 85% aqueous solution) were used as supplied. $H_3PO_4$ (230.6 g, 2 mole) was charged into a 3-necked 1-liter resin pot immersed in a 70°–75° C. water bath. $H_3BO_3$ (124 g, 2 mole) was added over about 5 minutes to the $H_3PO_4$ solution which was mechanically stirred. The resin pot was sealed with a condenser to inhibit water loss. Twenty five minutes after the complete addition of boric acid, 12.64 g of $NH_4HCO_3$ (0.16 mole) was added to the reaction mixture. Stirring was continued at 70°–75° C. for a total of 5 hours. After the first $3\frac{1}{2}$ hours, the condenser was removed to evaporate some of the by-product water. The resultant white paste was transferred to a crystallizing dish and spread into thin layers. The product was dried at 110° C. for 16 hours. The granulated product (20–35 mesh) was calcined at 400° C. for 2 hours in air before use as a dehydration catalyst.

Calcination conditions of ammonium carbonate modified catalysts impact on catalyst performance. The object of the calcination is to decompose the ammonium carbonate and thus yield a large pore. Thus, temperatures and times should be sufficient to achieve this decomposition while excessively high temperatures should be avoided.

Reactor System

The data for FIGS. 1–4 was obtained from a reactor system which was a 1.25 cm by 30 cm Pyrex ™ tube and a pump system for delivery of the 2MBA. The reactor also contained a 6 cm by 2 cm preheater filled with Pyrex ™ beads. Three thermocouples were situated in the catalyst bed; one in the preheater section, one in the first half of the catalyst bed and one in the lower half of the catalyst bed. The reactor was enclosed with fiberglass heating tapes and wrapped additionally with fiberglass tape. Automatic temperature controls were used on the three separate heaters so that each portion was independently heated and controlled. The reactor was thus run under essentially isothermal conditions.

A pump was used to charge the 2MBA feed continuously into the reactor in a downflow manner with a cocurrent nitrogen flow of 14 ml/minute. The effluent from the reactor was passed into a dry ice trap which served as the container for the reaction products. The reactor was run at atmospheric pressure. The nitrogen gas was used as a protective blanket for the catalyst, feed and effluent system. The nitrogen may also serve as a mild diluent and carrier gas although a nitrogen flow as low as 7 ml/minute changed very little in the reaction system.

The liquid hourly space velocity (LHSV) of 2MBA entering the preheater was set at 2.25 for all reactions. However, the LHSV can be varied. LHSV can be defined by more than one set of conditions. Therefore, as used herein, LHSV is the volume of liquid feed per hour that is passed over the total volume of catalyst. Total volume of catalyst is obtained by pouring the catalyst into a graduated cylinder to a mark of, for example, 40 cc's. The LHSV is simply calculated as follows:

$$LHSV = \frac{90 \text{ cc liquid feed/hour}}{40 \text{ cc catalyst}} = 2.25$$

The effluent (collected in the dry ice trap) from the reactor was analyzed with a gas chromatograph having a 7 meter column packed with a suitable material for resolving the components in the reaction mixture. Suitable packing materials, such as TCEP on Chromosorb P, are known to those skilled in analytical chemistry. Other conditions of the gas chromatograph were: detector temperature of 210° C., injection port temperature of 210° C., oven temperature program of 3 minutes at 70° C. followed by a 7.5° C./minute rise to 210° C. Standards were prepared and the response factors were determined for isoprene, 2-methyl-2-butene, 2-methyl-1-butene, 2-methylbutanal and methylisopropylketone with nonane as the weighed internal standard.

Since only the organic layer of the reaction effluent was analyzed, the weight of water produced must be calculated from the wt % of isoprene. The following mathematical adjustment was used:

(Wt % Isoprene) (Sample Wt) = Wt of Isoprene (Wt of Isoprene) (18/68) = Wt of Water Sample Wt + Wt of Water = Real Sample Wt (100) (Wt of Water/Real Sample Wt) = Real Wt % of Water Thus, (Wt % of Isoprene) (Sample Wt/Real Sample Wt) =

Real Wt % Isoprene; and (Wt % 2MBA) (Sample Wt/Real Sample Wt) =

Real Wt % 2MBA; then

% 2MBA Conversion =

$$\frac{(\% \text{ Purity of } 2MBA - \text{Real Wt } \% 2MBA)}{(\% \text{ Purity of } 2MBA)} \times 100;$$

% Isoprene Selectivity =

$$\frac{(\text{Real Wt } \% \text{ Isoprene} + \text{Real Wt } \% \text{ Water})}{(\% \text{ Purity of } 2MBA - \text{Real Wt } \% 2MBA)} \times 100$$

The 2MBA feed should be at least 90% pure. Other compounds in the 2MBA feed may include various by-products from the reaction of 2-butene and syngas to produce the 2MBA such as 2-methylbutyric acid. Other compounds such as n-pentanal may also be present in minor amounts.

Typical analysis of the effluent from the reactor using a catalyst of the invention after laboratory-scale fractionation had the following approximate product composition:

| Component | Weight % |
|---|---|
| n-butane | 0.11 |
| isobutene | 0.29 |
| trans-butene-2 | 0.07 |
| cis-butene-2 | 0.12 |
| pentene-1 | 0.02 |
| 2-methylbutene-1 | 0.42 |
| trans-pentene-2 | 0.04 |
| cis-pentene-2 | 0.05 |
| pentadiene-1,4 | 0.01 |
| 2-methylbutene-2 | 1.06 |
| isoprene | 97.68 |
| trans-pentadiene-1,3 | 0.06 |
| other | 0.07 |

Polymerization of Produced Isoprene

The reactor effluent after fractionation was used as a monomer to produce 1,4-polyisoprene using standard polymerization techniques. The isoprene polymerized in an acceptable manner and produced a polymer of expected properties.

Industrial Applicability

As demand for isoprene increases and the supply from petroleum feedstocks decrease, there will be a need for alternative methods of obtaining isoprene. The instant invention provides a process that utilizes a catalyst that overcomes the limitations previously found in the dehydration of 2MBA to isoprene. Thus, the industry now has a catalyst that is superior to the catalysts previously used. It is the unexpected and unobvious use of a boron phosphate catalyst as described and claimed herein that provides an advancement in the art of converting aldehydes to dienes.

Although the present invention has been described herein with reference to the preferred typical embodiments thereof, it will be apparent to those skilled in the art that there may be modifications made in the process hereof.

I claim:

1. An improved aldehyde dehydration catalyst, the improvement characterized in that boron phosphate is combined with from 0.1 to 10 mole percent ammonium carbonate or ammonium bicarbonate, based on moles of boron, and then calcined.

2. The catalyst of claim 1 wherein the calcination temperature is from 300°–500° C.

* * * * *